(12) United States Patent
Young

(10) Patent No.: US 7,571,649 B2
(45) Date of Patent: Aug. 11, 2009

(54) PROBE FOR INSPECTION OF EDGES OF A STRUCTURE

(75) Inventor: Fred D. Young, Bellevue, WA (US)

(73) Assignee: The Boeing Company, Chicago, IL (US)

( * ) Notice: Subject to any disclaimer, the term of this patent is extended or adjusted under 35 U.S.C. 154(b) by 280 days.

(21) Appl. No.: 11/680,191

(22) Filed: Feb. 28, 2007

(65) Prior Publication Data

US 2008/0202245 A1    Aug. 28, 2008

(51) Int. Cl.
*G01N 29/04* (2006.01)
(52) U.S. Cl. .......................................... 73/644; 73/635
(58) Field of Classification Search .................. 73/644, 73/634–638, 618–622, 641, 649
See application file for complete search history.

(56) References Cited

U.S. PATENT DOCUMENTS

| 3,028,753 A | 4/1962 | Joy |
| 3,420,097 A | 1/1969 | Battermann et al. |
| 5,473,943 A | 12/1995 | Schoenen et al. |
| 5,585,564 A * | 12/1996 | Brunty et al. ................. 73/634 |
| 5,585,565 A * | 12/1996 | Glascock et al. .............. 73/644 |
| 6,298,727 B1 * | 10/2001 | Fleming et al. ............... 73/644 |
| 6,722,202 B1 | 4/2004 | Kennedy et al. |
| 7,464,596 B2 * | 12/2008 | Bui et al. ...................... 73/618 |
| 2007/0175282 A1 | 8/2007 | Fetzer et al. |
| 2007/0239018 A1 | 10/2007 | Fetzer et al. |

FOREIGN PATENT DOCUMENTS

EP             1744156            1/2007

OTHER PUBLICATIONS

International Search Report on corresponding PCT application (PCT/US2008/055164) from International Searching Authority (EPO) dated Sep. 26, 2008.
Written Opinion on corresponding PCT application (PCT/US2008/055164) from International Searching Authority (EPO) dated Sep. 26, 2008.

* cited by examiner

*Primary Examiner*—Helen C. Kwok
(74) *Attorney, Agent, or Firm*—Klein, O'Neill & Singh, LLP

(57) ABSTRACT

An apparatus including a linear array transducer coupled to an upper housing of the apparatus and positioned above a tapered chamber. The tapered chamber configured to maintain a column of couplant between the linear array transducer and a structure to be inspected as the linear array transducer is positioned over an edge of the structure.

15 Claims, 4 Drawing Sheets

PROBE FOR INSPECTION OF EDGES OF A STRUCTURE

BACKGROUND

1. Field of the Invention

The present invention relates to examination probes and, more particularly, to ultrasonic probes.

2. Related Art

Non-destructive inspection is commonly used in the aircraft industry to inspect aircraft structures for any type of internal or external damage to the structure. Among the structures that are routinely non-destructively tested are composite structures.

An ultrasonic probe may be used to examine structures by transmitting ultrasonic signals to the structure and measuring a reflected signal returned by the structure to the probe. To facilitate the transmission of signals between conventional probes and the structure being examined, the structure is often wetted where the probe is to be applied with a coupling fluid (a "couplant"), such as water. The ultrasonic signals more easily transfer from the transducer to the structure by way of the couplant disposed between the probe and the structure.

When examining structures, it is often desired to examine edges of the structure. However, when a portion of conventional probes is moved over an edge, any coupling fluid that was disposed beneath the portion of the probe moved beyond the edge falls over the edge leaving no coupling fluid adjacent that portion. When coupling fluid is absent from the over-the-edge portion of the probe, the fluid between the probe and the item adjacent the edge will tend to also flow over the edge. When this happens, the probe is typically unable to accurately determine characteristics of the item adjacent the edge.

In one particular example, a delay line may be used in order to provide an edge inspecting capability. The delay line is typically a material, such as Rexolite or Plexiglass, which has acoustic impedance that is not the same as water. In operation, the probe is in contact with the delay line and the coupling fluid is applied between the probe and the delay line. The distance between the delay line and the surface of the part being inspected is normally between about 0.020" to 0.030". Water passageways are created, such as a series of small holes formed along the length of the delay line, to allow the coupling fluid to enter between the delay line and part surface. The surface tension of the coupling fluid is used to keep coupling fluid under the delay line as the probe traverses over the edge of the part surface.

This operation has many disadvantages. For example, the inspection speeds are slow, on the order of about 10 inches per second. Moreover, only "smooth" surfaces may be properly inspected, since it is difficult to maintain the coupling fluid over a rough surface. Finally, the acoustic mismatch between the delay line and the coupling fluid may alter the inspection frequency of the probe.

What is needed is an inspection apparatus and associated inspection method that improves the coupling of probes to items being examined allowing reliable, expedient, and accurate evaluation of item characteristics including at their edges.

SUMMARY

In light of the foregoing background, an improved apparatus and method for inspecting a structure, such as a composite structure are provided according to the various embodiments of the present invention.

In one aspect, an apparatus is provided for inspecting a structure. The apparatus includes a first housing defining at least one inlet for receiving a couplant. The apparatus also includes a second housing defining a tapered chamber and an inner chamber. The inner chamber is positioned to receive the couplant via the at least one inlet and dispense the couplant into the tapered chamber. A sensing element is coupled to the first housing and is positioned above the tapered chamber. The tapered chamber is configured to maintain a column of couplant between the sensing element and a structure to be inspected In yet another aspect, a method of inspection is provided including positioning a probe on a surface of a structure; moving the probe along the surface including over an edge of the surface; maintaining substantially a column of couplant between the probe and the surface while moving the probe over the edge of the surface.

BRIEF DESCRIPTION OF THE DRAWINGS

Figure 1:
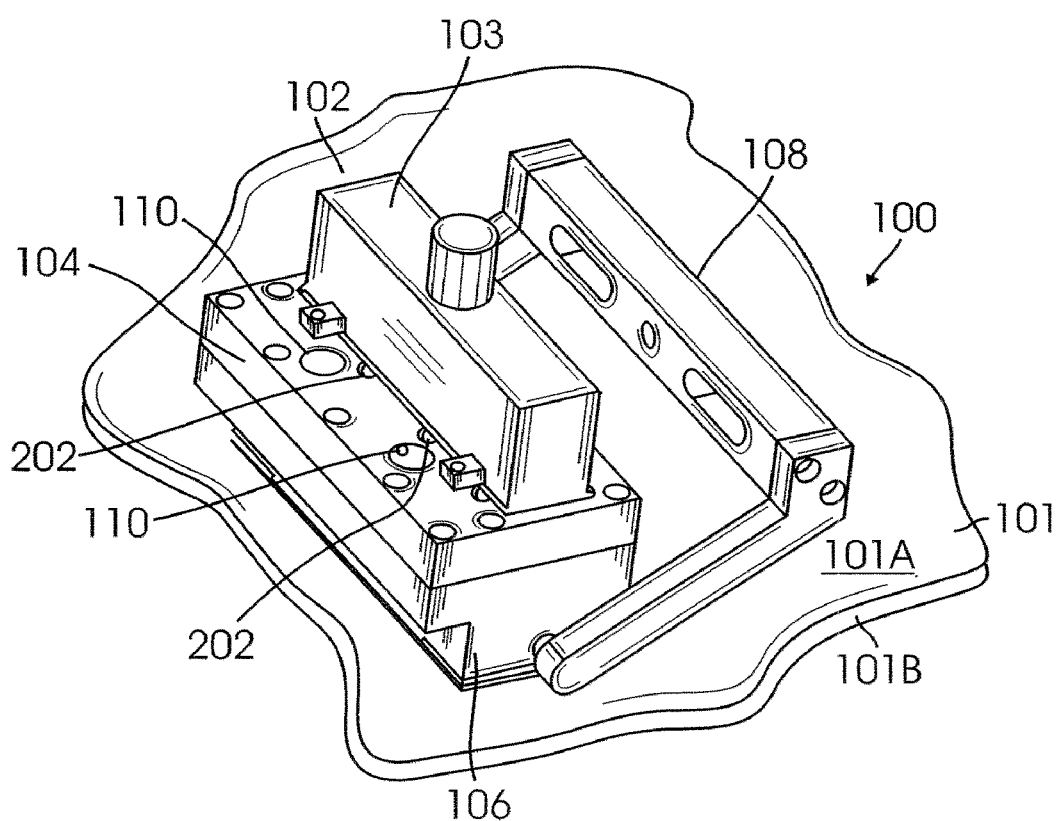
Figure 2:
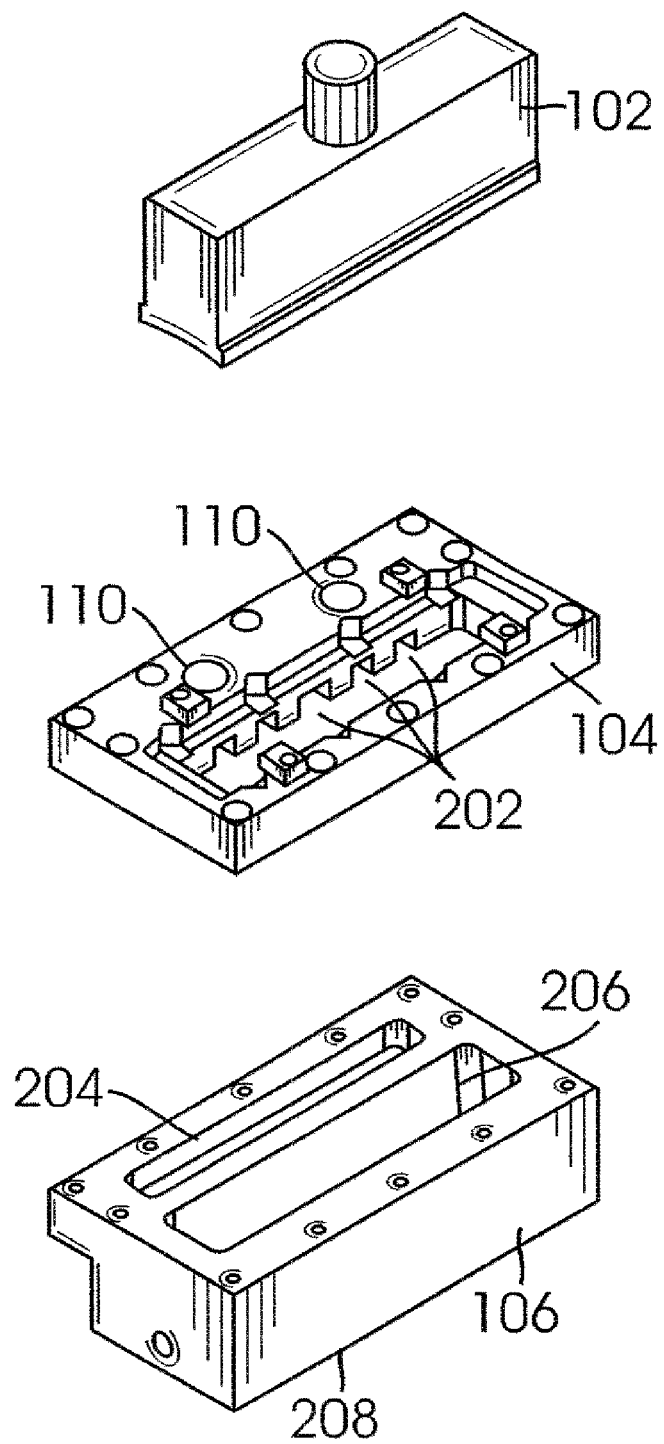
Figure 3:
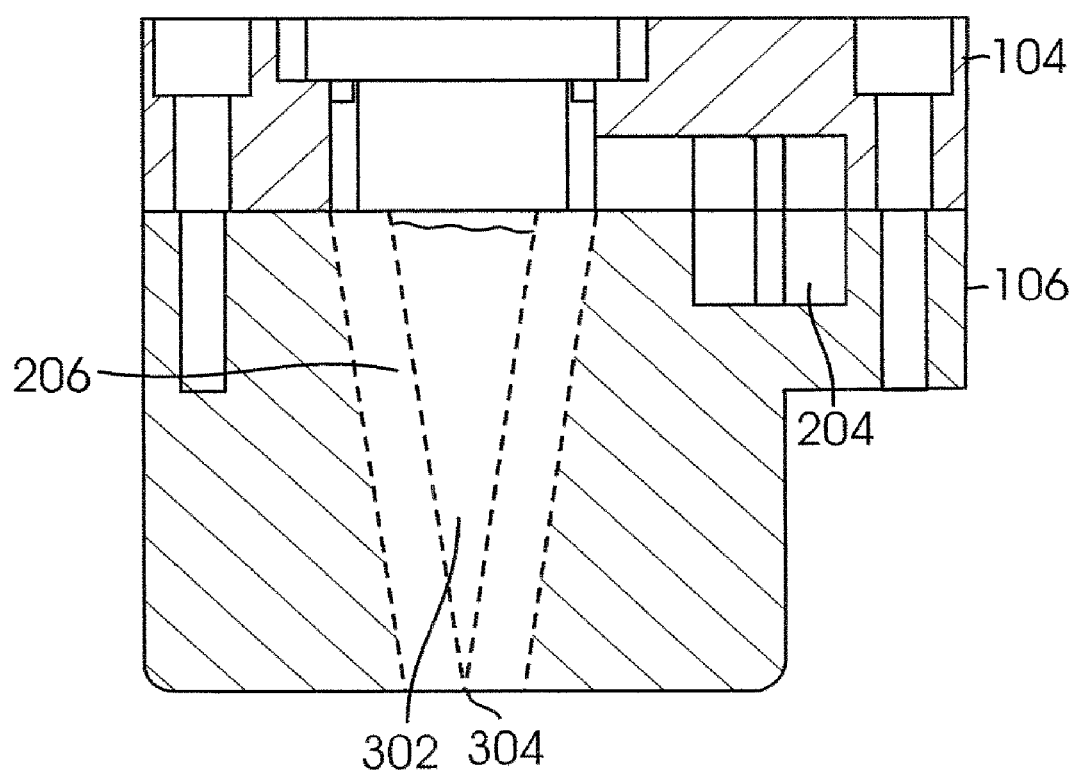
Figure 4:
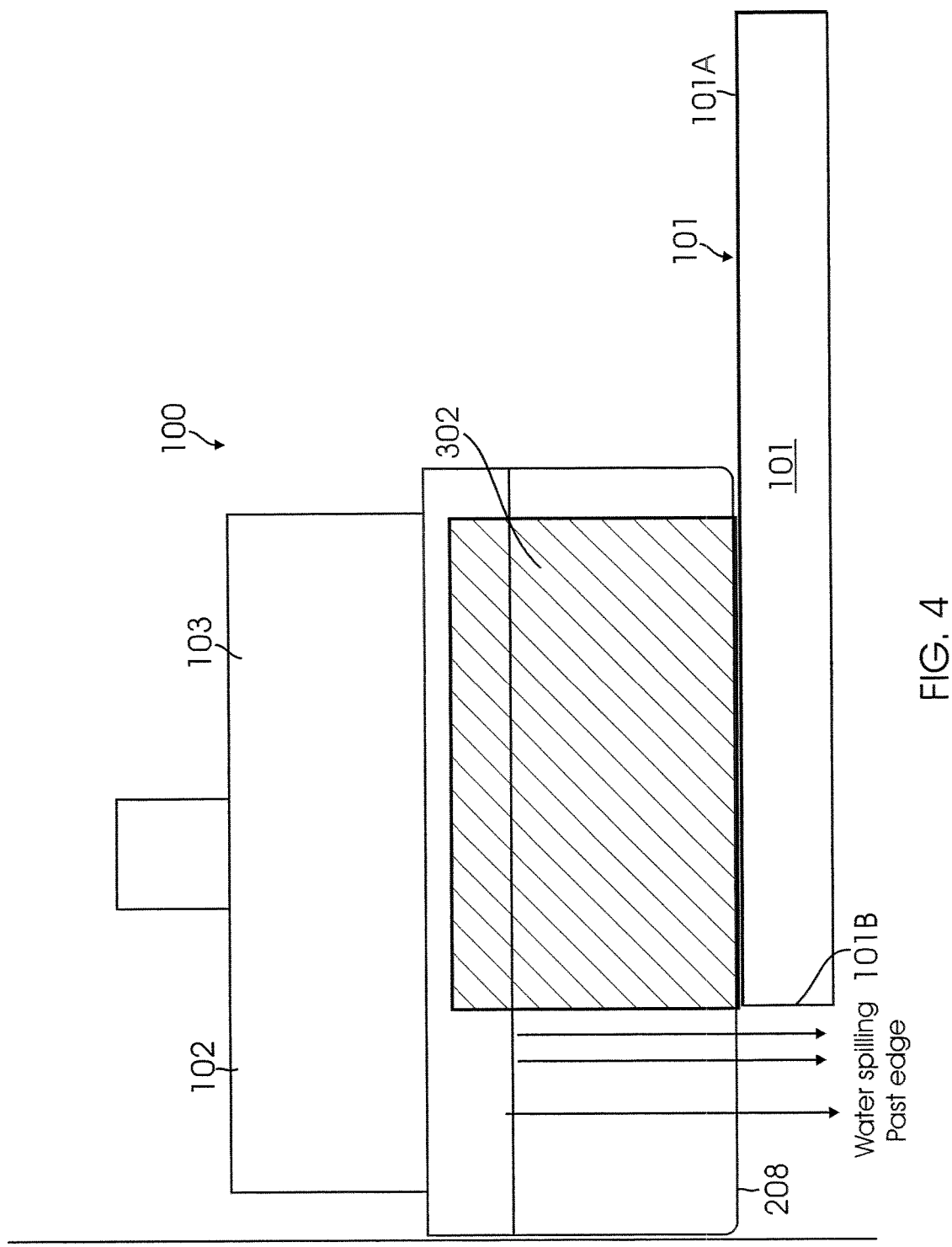

Having thus described the invention in general terms, reference will now be made to the accompanying drawings, which are not necessarily drawn to scale, and wherein:

FIG. 1 is a simplified perspective view of an inspection apparatus for inspection of a structure in accordance with one embodiment;

FIG. 2 is a simplified exploded view of components of the inspection apparatus in accordance with one embodiment;

FIG. 3 is a simplified cross-sectional view of the combined upper and lower housing components of the inspection apparatus in accordance with one embodiment; and FIG. 4 is a simplified frontal cross sectional view of the inspection apparatus as it traverses over a structure in accordance with an embodiment.

DETAILED DESCRIPTION

The disclosure now will be described more fully hereinafter with reference to the accompanying drawings, in which some, but not all embodiments are shown. Indeed, the disclosure may be embodied in many different forms and should not be construed as limited to the embodiments set forth herein. Like numbers refer to like elements throughout.

Referring now to FIG. 1, an apparatus 100 is illustrated for inspecting a structure 101 according to one embodiment of the present disclosure. Apparatus 100 can inspect a variety of structures formed of various materials. For example, structure 101 may be a composite structure, such as a honeycomb composite structure.

Structure 101 may have a myriad of shapes and sizes and may be used in a wide variety of applications, including in vehicular applications, such as in conjunction with aircraft, marine vehicles, automobiles, space craft and the like, as well as other non-vehicular applications, such as in conjunction with buildings and other construction projects. Moreover, structure 101 may be inspected prior to assembly or following assembly, as desired.

In one embodiment, apparatus 100 includes a probe 102, an upper housing 104, a lower housing 106 and a gimbaled handle 108. In one embodiment, upper housing 104 and lower housing 106 may be made of any suitable material, for example, Delrin®. Apparatus 100 is disposed proximate a first surface 101A of structure 101 to be inspected.

In one embodiment, apparatus 100 may be moved along the first surface 101A of structure 101 using various means, many of which are well know to those of skill in the art. In one embodiment, gimbaled handle 108 may be engaged by a robotic device (not shown) or the equivalent. As known to those skilled in the art, the robotic device can be controlled by a motion control system or other positioning system so as to controllably move probe 102 in a predefined manner and in accordance with a defined pattern along first surface 101A. Since apparatus 100 is in contact with and rides along first surface 101A, the motion control system or other positioning system need operate in a manner similar to that required by conventional scanning systems.

In one embodiment, probe 102, includes a sensing element 103 for inspecting structure 101 as probe 102 is moved over the respective surface 101A of structure 101. In one embodiment, sensing element 103 is positioned onto upper housing 104 such that the portion of sensing element 103 that faces the first surface 101A of structure 101 is spaced from the surface 208 (FIG. 2) of lower housing 106 that contacts first surface 101A.

During operation of probe 102, signals received by sensing element 103 of probe 102 may be stored along with an indication of the time at which the signals are received and/or an indication of the relative position of probe 102 when the signals are received. The signals may be stored by a memory device that is either co-located with probe 102 or remote from probe 102 and electrically coupled thereto. By analyzing the signals received by sensing element 103, the integrity of structure 101, as well as any flaws therein, may be determined.

While a single sensing element 103 is described, it should be understood that probe 102 may include an array of sensing elements 103, such as an array of ultrasonic transducers, thereby increasing the speed with which an inspection is performed and correspondingly reducing the cost associated with the inspection.

In one embodiment, sensing element 103 may include an ultrasonic transducer for ultrasonically inspecting structure 101 as probe 102 is moved over the respective surface of structure 101. For example, the ultrasonic transducer is operated in a reflection or pulse echo mode. Thus, the ultrasonic transducer both transmits and receives ultrasonic signals in this exemplary embodiment.

In order to facilitate the coupling of ultrasonic signals between the ultrasonic transducer of probe 102 and structure 101, a couplant, such as water or similar liquid, may be used. By bubbling liquid between the ultrasonic transducer and the respective surface of structure 101, the ultrasonic signals are effectively coupled into and out of structure 101.

As described in detail below, upper housing 104 may include inlets 110 for the couplant that is bubbled between the ultrasonic transducer and respective surface 101A of structure 101. Although not shown in the figures, a source of couplant may be connected to inlets 110. To facilitate this connection, a tube or equivalent structure, may be connected to upper housing 104 by any means, for example, by means of an interference or press fit of the tube into at least one of inlets 110.

As shown in FIG. 2, upper housing 104 defines inlets 110 and exit ports 202. Lower housing 106 defines inner chamber 204 formed adjacent couplant chamber 206 (hereinafter "chamber 206"), which is in fluid communication with that portion of sensing element 103 that faces the first surface 101A of structure 101.

Couplant that is introduced through inlets 110 flows via internal channels into inner chamber 204 where the couplant initially collects as it enters upper housing 104. As inner chamber 204 fills with couplant, the couplant spills out from inner chamber 204 and flows though exit ports 202 into chamber 206.

Advantageously, by initially collecting the couplant into inner chamber 204, the turbulence of the couplant flow is reduced. This allows the couplant to flow smoothly between sensing element 103 and first surface 101A with no bubbles, cavitation or other turbulence that could otherwise detrimentally affect the signal to noise ratio.

FIG. 3 is a cross-sectional view of upper hosing 104 and lower housing 106, combined. As shown in FIG. 3, chamber 206 is tapered to form a "V"-shaped chamber to help maintain a "column" of couplant 302 within chamber 206 to effectively fill the area between sensing element 103 and first surface 101A. The tapered shape of chamber 206 restricts the flow of couplant 302 as it flows through opening 304. The funnel effect is applied along the length of probe 102. Once chamber 206 fills, the excess couplant along with any air that is in the chamber, is forced out through exit ports 202.

In operation, as shown in FIG. 4, apparatus 100 is disposed proximate to first surface 101A of structure 101. In this manner, probe 102 may advantageously be disposed in probing contact with the respective surfaces of structure 101.

By permitting contact between apparatus 100 via contact surface 208 and the respective surface 101A of structure 101, the orientation of probe 102 and, more particularly, sensing element 103, such as the ultrasonic transducer, may be maintained without requiring the orientation of probe 102 to be controlled by means of a complex motion control system or other type of positioning system.

Additionally, the contact between apparatus 100 via contact surface 208 and the respective surface 101A of structure 101 maintains a consistent spacing between the respective sensing element 103, such as the respective ultrasonic transducers, and structure 101, similarly without requiring complex motion control systems or other positioning systems.

A couplant, such as water, is then bubbled through inlets 110 (FIG. 1) of upper housing 104. The couplant then flows from inlets 110 into inner chamber 204 (FIG. 2), where the couplant is initially collected. The couplant then flows out from inner chamber 204 through exit ports 202 (FIG. 2) and into chamber 206. The V-shaped chamber 206 fills with couplant to create a column of couplant 302 between sensing element 103 and the respective surface 101A of structure 101.

Referring again to FIG. 4, in one embodiment, as probe 102 of apparatus 100 approaches an edge 101B of structure 101, probe 102 may be allowed to overhang edge 101B. In this embodiment, because of the V-shape of chamber 206, the column of couplant 302 is maintained between sensing element 103 and first surface 101A even though couplant 302 is allowed to spill over edge 101B. In this manner, when probe 102 is 90 degrees to edge 101B, the coupling of signals, for example, ultrasonic signals, between probe 102 and structure 101 is maintained at edge 101B. In this embodiment, apparatus 100 may use couplant 302 as a liquid bearing to facilitate the movement of apparatus 100 over first surface 101A.

It is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An apparatus for inspecting a structure comprising:
    a first housing defining at least one inlet for receiving a couplant;
    a second housing defining a tapered chamber and an inner chamber, said inner chamber positioned to receive said couplant via said at least one inlet and dispense said couplant into said tapered chamber; and
    a sensing element coupled to said first housing, said sensing element positioned above said tapered chamber, said tapered chamber configured to restrict the flow of said couplant as it flows out through an opening in said tapered chamber to maintain a column of couplant between said sensing element and an edge of a planar structure to be inspected as at least a portion of the sensing element overhangs the edge of the planar structure to be inspected.

2. The apparatus of claim 1, wherein said couplant comprises water.

3. The apparatus of claim 1, wherein said first housing and said second housing comprise Delrin®.

4. The apparatus of claim 1, wherein said sensing element comprises an ultrasonic transducer.

5. The apparatus of claim 1, wherein said sensing element comprises an array of ultrasonic transducers.

6. The apparatus of claim 1, wherein said first housing further defines exit ports formed to allow said couplant to flow from said inner chamber and into said tapered chamber with reduced turbulence.

7. The apparatus of claim 1, wherein said structure comprises a composite honeycomb structure.

8. An apparatus for inspecting a structure comprising:
an upper housing defining at least one inlet for receiving a flow of water;
a lower housing defining a tapered chamber and an inner chamber, said inner chamber positioned to receive said water via said at least one inlet and dispense said water into said tapered chamber; and
a linear array transducer coupled to said upper housing, said linear array transducer positioned above said tapered chamber, said tapered chamber configured to restrict the flow of said couplant as it flows out through an opening in said tapered chamber to maintain a column of water between said linear array transducer and an edge of a planar structure to be inspected as at least a portion of the linear array transducer is positioned to overhang an edge of the planar structure.

9. The apparatus of claim 8, wherein said upper housing and said lower housing comprise Delrin®.

10. The apparatus of claim 8, wherein said upper housing further defines exit ports formed to allow said water to flow from said inner chamber and into said tapered chamber with reduced turbulence.

11. The apparatus of claim 8, wherein said structure comprises a composite honeycomb structure.

12. A method of inspection comprising:
positioning a probe having a sensing element on a surface of a planar structure having an edge;
moving the probe along the surface until a portion of the sensing element overhangs beyond the edge of the planar surface; and
maintaining substantially a column of couplant between said sensing element and said edge of the planar surface while the sensing element overhangs beyond the edge of the planar surface.

13. The method of claim 12, wherein said couplant comprises water.

14. The method of claim 12, wherein maintaining substantially the column of couplant between said probe and said surface while moving over the edge of the surface comprises transmitting signals into and receiving signals from the structure at various locations.

15. The method of claim 14, wherein said various locations comprises an edge of the structure.

* * * * *